United States Patent
Shigeto et al.

(10) Patent No.: US 10,098,583 B2
(45) Date of Patent: Oct. 16, 2018

(54) SLEEP QUALITY ESTIMATION DEVICE, SLEEP QUALITY ESTIMATION METHOD AND PROGRAM FOR SLEEP QUALITY ESTIMATION

(75) Inventors: Kazuhide Shigeto, Susono (JP); Hiroki Okamura, Susono (JP); Hirokazu Kikuchi, Hadano (JP)

(73) Assignee: TOYOTA JIDOSHA KABUSHIKI KAISHA, Toyota-shi, Aich (JP)

( * ) Notice: Subject to any disclaimer, the term of this patent is extended or adjusted under 35 U.S.C. 154(b) by 1047 days.

(21) Appl. No.: 14/379,458

(22) PCT Filed: Feb. 24, 2012

(86) PCT No.: PCT/JP2012/054661
§ 371 (c)(1),
(2), (4) Date: Aug. 18, 2014

(87) PCT Pub. No.: WO2013/125048
PCT Pub. Date: Aug. 29, 2013

(65) Prior Publication Data
US 2015/0038865 A1   Feb. 5, 2015

(51) Int. Cl.
*A61B 5/00* (2006.01)
*A61B 5/113* (2006.01)
*A61B 5/08* (2006.01)

(52) U.S. Cl.
CPC .......... *A61B 5/4815* (2013.01); *A61B 5/0816* (2013.01); *A61B 5/1135* (2013.01);
(Continued)

(58) Field of Classification Search
None
See application file for complete search history.

(56) References Cited

U.S. PATENT DOCUMENTS

2004/0230398 A1   11/2004   Okada et al.
2005/0042589 A1*   2/2005   Hatlestad ............ A61B 5/0031
                                                           434/262
(Continued)

FOREIGN PATENT DOCUMENTS

JP   2004-358235 A   12/2004

OTHER PUBLICATIONS

M. Bsoul et al., "Real-Time Sleep Quality Assessment Using Single-Lead ECG and Multi-Stage SVM Classifier", 2010 Annual International Conference of the IEEE Engineering in Medicine and Biology Society, Buenos Aires, Argentina, Aug. 31, 2010, p. 1178-1181, XP032108070.

(Continued)

*Primary Examiner* — Jacqueline Cheng
*Assistant Examiner* — Jairo Portillo
(74) *Attorney, Agent, or Firm* — Sughrue Mion, PLLC

(57) ABSTRACT

In a sleep quality estimation device, a respiration sensor detects the respiratory waveform of a subject. A sleep stage estimation unit estimates the sleep stage of the subject during sleep based on the respiratory waveform detected by the respiration sensor. In a sleep rhythm model database, models associated with the appearance probability of δ-wave for the sleep stage during sleep are recorded. A sleep quality estimation unit estimates the appearance time of δ-wave of the subject during sleep based on the sleep stage of the subject estimated by the sleep stage estimation unit and the models associated with the appearance probability of δ-wave for the sleep stage recorded in the sleep rhythm model database, and estimates the sleep quality of the subject based on the appearance time of δ-wave.

5 Claims, 8 Drawing Sheets

(52) U.S. Cl.
CPC .......... *A61B 5/4812* (2013.01); *A61B 5/7264* (2013.01); *A61B 5/7278* (2013.01); *A61B 2503/22* (2013.01)

(56) References Cited

U.S. PATENT DOCUMENTS

| | | | |
|---|---|---|---|
| 2006/0205994 A1* | 9/2006 | Sunnen ................. | A61M 21/00 600/27 |
| 2006/0229335 A1* | 10/2006 | Teegarden ............ | C07D 231/12 514/314 |
| 2008/0195166 A1* | 8/2008 | Sun ...................... | A61B 5/0478 607/18 |
| 2012/0323085 A1* | 12/2012 | Takeda ................. | A61B 5/4815 600/300 |

OTHER PUBLICATIONS

Dorfman Furman G et al, "Electrocardiogram derived respiration during sleep", Computers in Cardiology, Sep. 25, 2005, vol. 32, p. 351-354, XP010889845.

* cited by examiner

Fig.8

| CYCLE (CYCLE) | C1 | C2 | C3 | C4 |
|---|---|---|---|---|
| TIME (MINUTE) | 90 MINUTES | 180 MINUTES | 270 MINUTES | 360 MINUTES |
| STANDARD | S1 | S2 | S3 | S4 |
| δ-WAVE APPEARANCE PROBABILITY IN MODEL(%) | 65 | 20 | 10 | 5 |

SLEEP QUALITY ESTIMATION DEVICE, SLEEP QUALITY ESTIMATION METHOD AND PROGRAM FOR SLEEP QUALITY ESTIMATION

CROSS REFERENCE TO RELATED APPLICATIONS

This application is a National Stage of International Application No. PCT/JP2012/054661 filed Feb. 24, 2012, the contents of which are incorporated herein by reference in their entirety.

TECHNICAL FIELD

An embodiment of the present invention relates to a sleep quality estimation device, a sleep quality estimation method, and a program for sleep quality estimation, and in particular, to a sleep quality estimation device and a sleep quality estimation method which estimate the sleep quality of a subject from a physiological index of the subject.

BACKGROUND ART

A method which simply estimates the sleep quality during sleep has been suggested in, for example, Patent Literature 1 or the like. In the method of Patent Literature 1, a sleep state is estimated from a physiological index. In the method of Patent Literature 1, the rhythm of sleep of a subject is estimated from the appearance probability of a specific sleep stage per unit time. In the method of Patent Literature 1, the sleep quality, such as "sleep rhythm", "head relaxation", and "quick falling asleep", is estimated using the rhythm of sleep of the subject. A sleep stage II and subsequent stages become SWS (deep sleep), and the sleep quality is estimated from the appearance probability of SWS. In the method of Patent Literature 1, for example, when an evaluation element is "head relaxation", a period during which the appearance ratio of SWS increases from 0% after going to bed, the appearance ratio of SWS exceeds a predetermined threshold level S1, such as 40%, and becomes 0% again, and then, the appearance ratio of SWS increases becomes one cycle. In the method of Patent Literature 1, an evaluation point is calculated according to the total of the appearance ratio of SWS within one cycle for every cycle, and the sum of the evaluation points of the respective cycles becomes the evaluation of "head relaxation".

CITATION LIST

Patent Literature
[Patent Literature 1] Japanese Unexamined Patent Application Publication No. 2004-358235

SUMMARY OF INVENTION

Technical Problem

The technique of Patent Literature 1 evaluates the sleep quality based on the appearance ratio of deep sleep during sleep and the accumulated appearance time. However, if the sleep quality of the subject is evaluated by this method, there may be a large error from the actual quality of sleep of the subject. For this reason, various improvements are required.

An embodiment of the invention has been accomplished in consideration of the above-described problem, and an object of the invention is to provide a sleep quality estimation device, a sleep quality estimation method, and a program for sleep quality estimation capable of estimating the sleep quality of a subject with higher precision.

Solution to Problem

A sleep quality estimation device according to an embodiment of the invention includes a physiological index detection unit which detects a physiological index of a subject, a sleep depth estimation unit which estimates the depth of sleep of the subject during sleep based on the index detected by the physiological index detection unit, and a sleep quality estimation unit which estimates the appearance time of δ-wave of the subject during sleep from the depth of sleep of the subject during sleep estimated by the sleep depth estimation unit and estimates the sleep quality of the subject based on the appearance time of δ-wave.

With this configuration, in the sleep quality estimation device, the physiological index detection unit detects the physiological index of the subject. The sleep depth estimation unit estimates the depth of sleep of the subject during sleep based on the index detected by the physiological index detection unit. The sleep quality estimation unit estimates the appearance time of δ-wave of the subject during sleep from the depth of sleep of the subject during sleep estimated by the sleep depth estimation unit and estimates the sleep quality of the subject based on the appearance time of δ-wave. For this reason, it is possible to estimate the sleep quality of the subject with higher precision based on the appearance time of δ-wave more closely related to the sleep quality compared to a method which simply accumulates a deep sleep time zone to estimate the sleep quality.

In this case, the physiological index detection unit may detect the respiration of the subject as the physiological index of the subject.

With this configuration, the physiological index detection unit detects the respiration of the subject as the physiological index of the subject. Since the respiration can be detected in a noncontact state with the skin of the subject, unlike brain wave or heartbeat, it becomes possible to improve the convenience of the subject or to simplify the configuration of the device.

A sleep quality estimation device according to another embodiment of the invention includes a sleep depth information acquisition unit which acquires time series information relating to the depth of sleep of a subject during sleep, and a sleep quality estimation unit which estimates the appearance time of δ-wave of the subject during sleep from the depth of sleep of the subject during sleep according to the time series information acquired by the sleep depth information acquisition unit and estimates the sleep quality of the subject based on the appearance time of δ-wave.

With this configuration, the sleep depth information acquisition unit acquires the time series information relating to the depth of sleep of the subject during sleep, and the sleep quality estimation unit estimates the appearance time of δ-wave of the subject during sleep from the depth of sleep of the subject during sleep according to the time series information acquired by the sleep depth information acquisition unit and estimates the sleep quality of the subject based on the appearance time of δ-wave. For this reason, even if the physiological index of the subject is not necessarily measured by the device itself or the depth of sleep of the subject is not necessarily estimated, it is possible to estimate the sleep quality of the subject.

The sleep quality estimation device may further include a database in which models associated with the appearance probability of δ-wave for the depth of sleep during sleep are recorded, and the sleep quality estimation unit may estimate the appearance time of δ-wave of the subject during sleep based on the depth of sleep of the subject during sleep and the models associated with the appearance probability of δ-wave for the depth of sleep during sleep recorded in the database and may estimate the sleep quality of the subject based on the appearance time of δ-wave.

With this configuration, the sleep quality estimation unit estimates the appearance time of δ-wave of the subject during sleep based on the depth of sleep of the subject during sleep and the models associated with the appearance probability of δ-wave for the depth of sleep during sleep recorded in the database and estimates the sleep quality of the subject based on the appearance time of δ-wave. For this reason, it is possible to estimate the appearance time of δ-wave with higher precision using the models and to estimate the sleep quality of the subject with higher precision.

In this case, the models recorded in the database may be associated with the appearance probability of δ-wave for a stay time when the depth of sleep of each sleep cycle from non-REM sleep to REM sleep stays with a value deeper than a predetermined value, and the sleep quality estimation unit may estimate the stay time of each sleep cycle from the depth of sleep of the subject during sleep and may estimate the appearance time of δ-wave of the subject during sleep based on the stay time and the models associated with the appearance probability of δ-wave for the stay time of each sleep cycle.

With this configuration, the models recorded in the database are associated with the appearance probability of δ-wave for a stay time when the depth of sleep of each sleep cycle from non-REM sleep to REM sleep stays with a value deeper than a predetermined value, and the sleep quality estimation unit estimates the stay time of each sleep cycle from the depth of sleep of the subject during sleep and estimates the appearance time of δ-wave of the subject during sleep based on the stay time and the models associated with the appearance probability of δ-wave for the stay time of each sleep cycle. There is the stay time when the depth of sleep stays with a deep value for each sleep cycle from non-REM sleep to REM sleep, and the appearance probability of δ-wave for the stay time differs for each sleep cycle. For this reason, the appearance time of δ-wave is estimated based on the models associated with the appearance probability of δ-wave for the stay time of each sleep cycle, whereby it is possible to estimate the appearance time of δ-wave and to estimate the sleep quality of the subject with higher precision.

In this case, in the models recorded in the database, the longer the elapsed time during sleep is, the lower the appearance probability of δ-wave for the stay time may be set.

In human sleep, as the elapsed time during sleep is long, the appearance probability of δ-wave for the stay time decreases. For this reason, a model in which, the longer the elapsed time during sleep is, the lower the appearance probability of δ-wave for the stay time is set is used, whereby it is possible to estimate the sleep quality with higher precision by a model more conforming to reality.

A sleep quality estimation method according to still another embodiment of the invention includes a physiological index detection step of detecting a physiological index of a subject, a sleep depth estimation step of estimating the depth of sleep of the subject during sleep based on the index detected in the physiological index detection step, and a sleep quality estimation step of estimating the appearance time of δ-wave of the subject during sleep from the depth of sleep of the subject during sleep estimated in the sleep depth estimation step and estimating the sleep quality of the subject based on the appearance time of δ-wave.

In this case, in the physiological index detection step, the respiration of the subject may be detected as the physiological index of the subject.

A sleep quality estimation method according to still another embodiment of the invention includes a sleep depth information acquisition step of acquiring time series information relating to the depth of sleep of a subject during sleep, and a sleep quality estimation step of estimating the appearance time of δ-wave of the subject during sleep from the depth of sleep of the subject during sleep according to the time series information acquired in the sleep depth information acquisition step and estimating the sleep quality of the subject based on the appearance time of δ-wave.

In the sleep quality estimation step, the appearance time of δ-wave of the subject during sleep may be estimated based on the depth of sleep of the subject during sleep and the models associated with the appearance probability of δ-wave for the depth of sleep during sleep recorded in a database and the sleep quality of the subject may be estimated based on the appearance time of δ-wave.

In this case, the models recorded in the database may be associated with the appearance probability of δ-wave for a stay time when the depth of sleep of each sleep cycle from non-REM sleep to REM sleep stays with a value deeper than a predetermined value, and in the sleep quality estimation step, the stay time of each sleep cycle may be estimated from the depth of sleep of the subject during sleep and the appearance time of δ-wave of the subject during sleep may be estimated based on the models associated with the appearance probability of δ-wave for the stay time of each sleep cycle.

In this case, in the models recorded in the database, the longer the elapsed time during sleep is, the lower the appearance probability of δ-wave for the stay time may be set.

According to still another embodiment of the invention, there is provided a program for sleep quality estimation which causes a computer to execute a sleep depth information acquisition step of acquiring time series information relating to the depth of sleep of a subject during sleep, and a sleep quality estimation step of estimating the appearance time of δ-wave of the subject during sleep from the depth of sleep of the subject during sleep according to the time series information acquired in the sleep depth information acquisition step and estimating the sleep quality of the subject based on the appearance time of δ-wave.

In this case, the sleep quality estimation step may cause the computer to estimate the appearance time of δ-wave of the subject during sleep based on the depth of sleep of the subject during sleep and the models associated with the appearance probability of δ-wave for the depth of sleep during sleep recorded in a database and may cause the computer to estimate the sleep quality of the subject based on the appearance time of δ-wave.

In this case, the models recorded in the database may be associated with the appearance probability of δ-wave for a stay time when the depth of sleep of each sleep cycle from non-REM sleep to REM sleep stays with a value deeper than a predetermined value, and the sleep quality estimation step may cause the computer to estimate the stay time of each sleep cycle from the depth of sleep of the subject during sleep and may cause the computer to estimate the appearance time of δ-wave of the subject during sleep based on the models associated with the appearance probability of δ-wave for the stay time of each sleep cycle.

In this case, in the models recorded in the database, the longer the elapsed time during sleep is, the lower the appearance probability of δ-wave for the stay time may be set.

Advantageous Effects of Invention

With the sleep quality estimation device, the sleep quality estimation method, and the program for sleep quality estimation according to the embodiment of the invention, it is possible to estimate the sleep quality of the subject with higher precision.

BRIEF DESCRIPTION OF DRAWINGS

FIG. 8 is a table showing the appearance probability of δ-wave in a standard sleep rhythm model.

DESCRIPTION OF EMBODIMENTS

Figure 1:
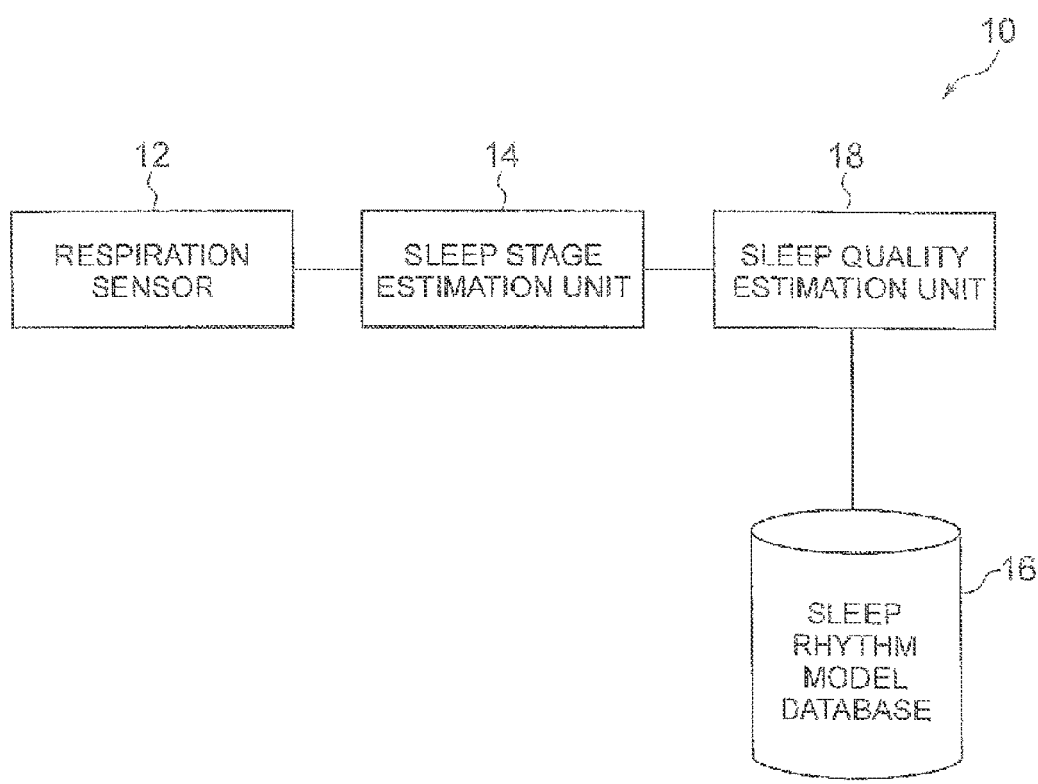
FIG. 1 is a block diagram showing the configuration of a sleep quality estimation device according to an embodiment.

Hereinafter, an embodiment of the invention will be described in detail referring to the drawings. A sleep quality estimation device of this embodiment is a device which is mounted in a vehicle to estimate the sleep quality of a driver after a nap and is provided in a lodging facility, in a medical institution, or at home to estimate the sleep quality of a subject. As shown in FIG. 1, a sleep quality estimation device 10 of this embodiment includes a respiration sensor 12, a sleep stage estimation unit 14, a sleep rhythm model database 16, and a sleep quality estimation unit 18.

The respiration sensor 12 is constituted by a piezoelectric element or the like. The respiration sensor 12 is mounted on clothing, such as a trousers belt of the subject. The respiration sensor 12 detects respiratory waveform, which is the operation of a chest or an abdomen of the subject, as one of physiological indexes of the subject. In addition to the respiration of the subject, as the physiological index of the subject, brain wave, heartbeat, or other body motions may be detected. However, the respiration of the subject is superior in that the respiration can be detected in a noncontact state with the skin of the subject without brining sensors, such as multiple electrodes, into contact with the skin of the subject.

The sleep stage estimation unit 14 is constituted by a computer including a CPU (Central Processing Unit), a ROM (Read Only Memory), a RAM (Random Access Memory), and the like as hardware. The function of the sleep stage estimation unit 14 is realized by the computer executing processing described below by a program for sleep quality estimation of this embodiment. The sleep stage estimation unit 14 estimates the sleep stage of the subject based on the respiratory waveform of the subject detected by the respiration sensor 12 using a method described below. The sleep stage estimation unit 14 estimates the sleep stage of the subject among sleep stages I to IV. However, the sleep stage of the subject estimated by the sleep stage estimation unit 14 is not necessarily strict. The precision of the sleep stage of the subject estimated by sleep stage estimation unit 14 may be such an extent that the time when the sleep stage of the subject stays in a stage deeper than the sleep stage II, in which δ-wave appears for each sleep cycle from non-REM sleep to REM sleep can be recognized.

The sleep rhythm model database 16 is realized by hardware, such as a HDD (Hard Disk Drive), in which information is recorded. As described below, the sleep rhythm model database 16 records standard models which define the appearance probability of δ-wave for a stay time when a sleep stage of each sleep cycle from non-REM sleep to REM sleep stays with a value (minimum value) deeper than a predetermined value in the standard statistics of an unspecified number of subjects. In this embodiment, in order to estimate the sleep quality specialized for a specific subject, in the sleep rhythm model database 16, the appearance probability of δ-wave for the stay time when a sleep stage of each sleep cycle of the specific subject stays with a value deeper than a predetermined value may be defined based on measured values accumulated for the specific subject.

The sleep quality estimation unit 18 is constituted by a computer including a CPU, a ROM, a RAM, and the like as hardware. The function of the sleep quality estimation unit 18 is realized by the computer executing processing described below by the program for sleep quality estimation of this embodiment. As described below, the sleep quality estimation unit 18 estimates the stay time which is the time for staying in a stage deeper than the sleep stage II of each sleep cycle from the sleep stage of the subject during sleep estimated by the sleep stage estimation unit 14. The sleep quality estimation unit 18 estimates the appearance time of δ-wave of the subject during sleep based on the estimated stay time and the models associated with the appearance probability of δ-wave for the stay time of each sleep cycle recorded in the sleep rhythm model database 16 and estimates the sleep quality of the subject based on the accumulated time of the appearance time of δ-wave.

Figure 2:
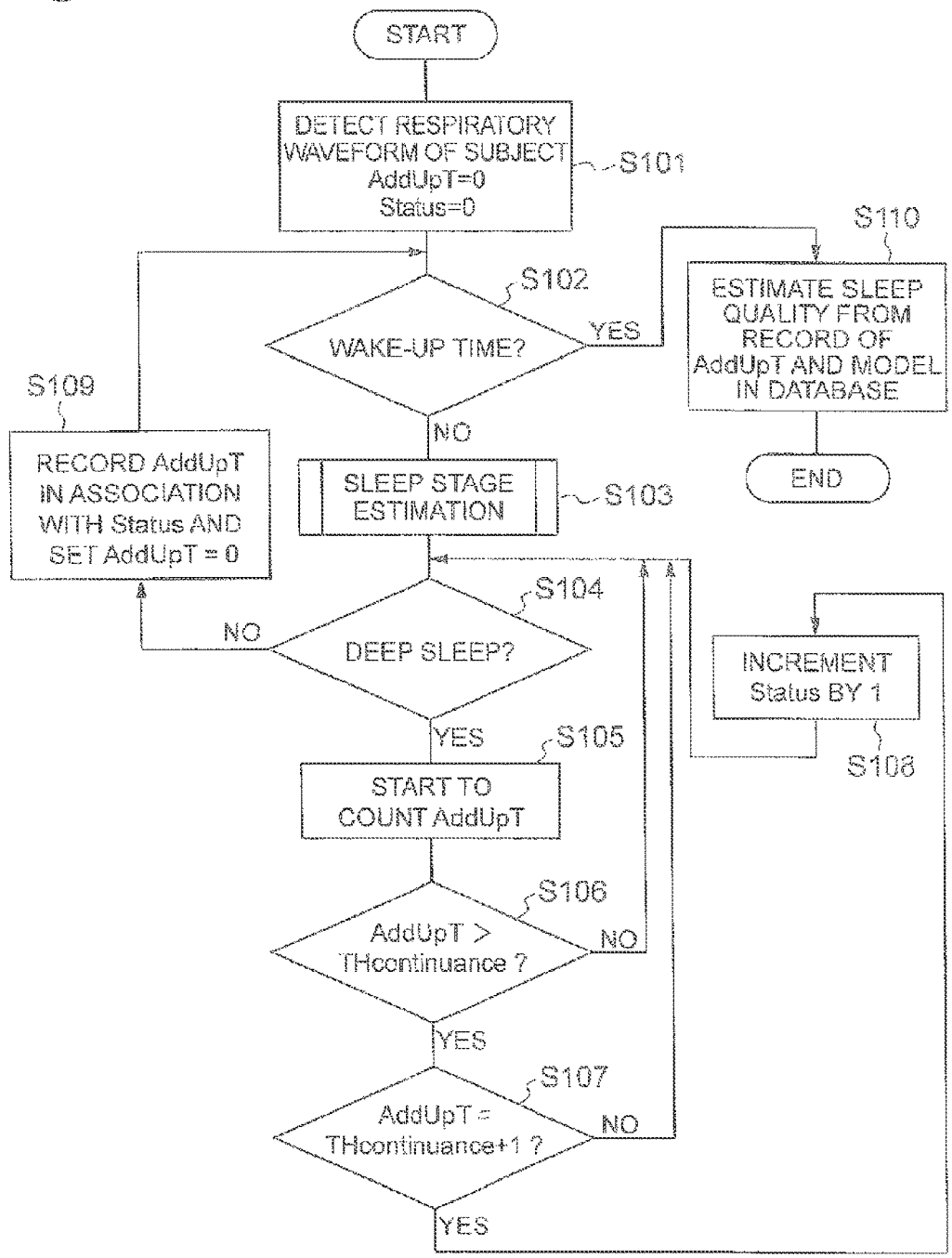
FIG. 2 is a flowchart showing the operation of the sleep quality estimation device according to the embodiment.

Hereinafter, the operation of the sleep quality estimation device 10 of this embodiment will be described. As shown in FIG. 2, the sleep quality estimation unit 18 of the sleep quality estimation device 10 resets, to 0, AddUpT which is the stay time in a sleep stage deeper than the sleep stage II and Status which is the total number of turns of the cycle of deep sleep, and detects the respiratory waveform of the subject (S101). The sleep quality estimation unit 18 performs determination about whether or not the wake-up time of the subject is reached (S102). When the wake-up time is not reached (S102), the sleep stage estimation unit 14 of the sleep quality estimation device 10 estimates the sleep stage of the subject (S103).

Figure 3:
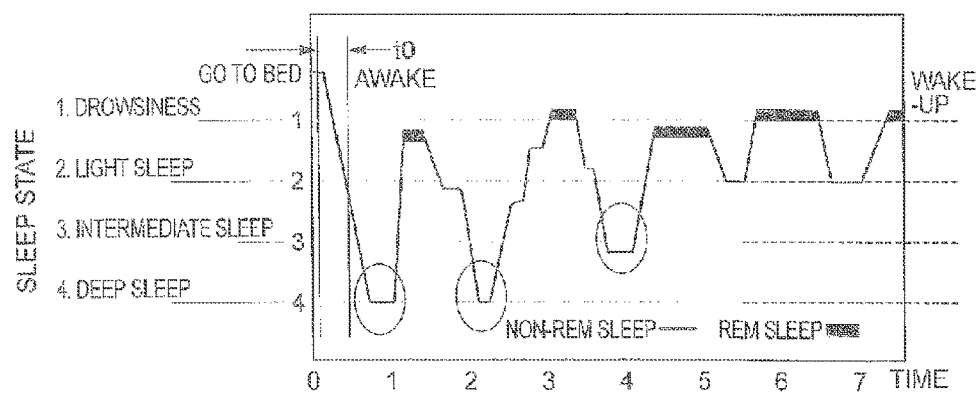
FIG. 3 is a graph showing a general cycle of transition of sleep stages in a night.

As shown in FIG. 3, in general, the sleep stage during sleep reaches a stage deeper than sleep stage II about at the time t0 after going to bed. In this case, sleep is non-REM sleep. Then, after the stay time of deep sleep of the sleep stage IV has elapsed, the sleep stage reaches a time zone of light sleep of REM sleep. A period of about 90 minutes from non-REM sleep to REM sleep is referred to as a sleep cycle or an ultradian cycle. Thereafter, REM sleep, the stay time of deep sleep, and non-REM sleep are repeated in the same cycle of about 90 minutes. The sleep stage becomes gradually light and reaches wake-up.

Figure 4:
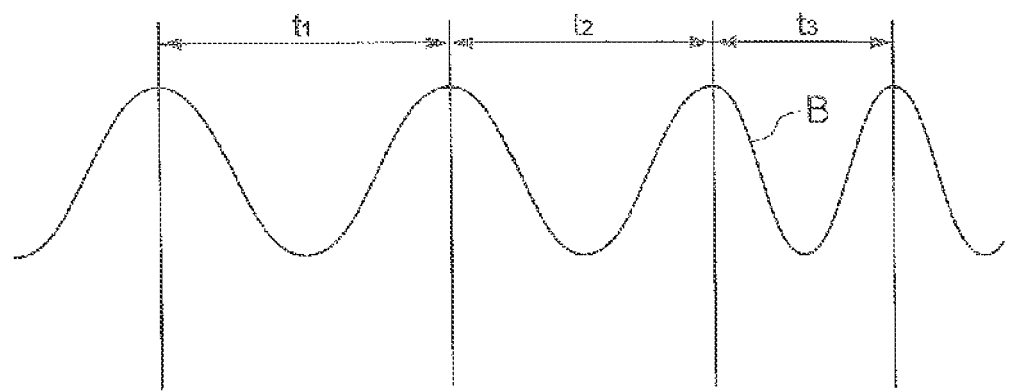
FIG. 4 is a diagram showing a respiratory waveform measured by a respiration sensor.
Figure 5:
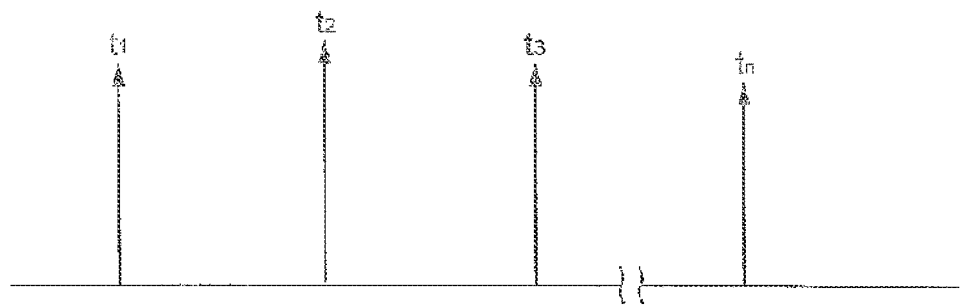
FIG. 5 is a diagram showing a result of sampling the time of each wavelength of the respiratory waveform of the FIG. 4.
Figure 6:
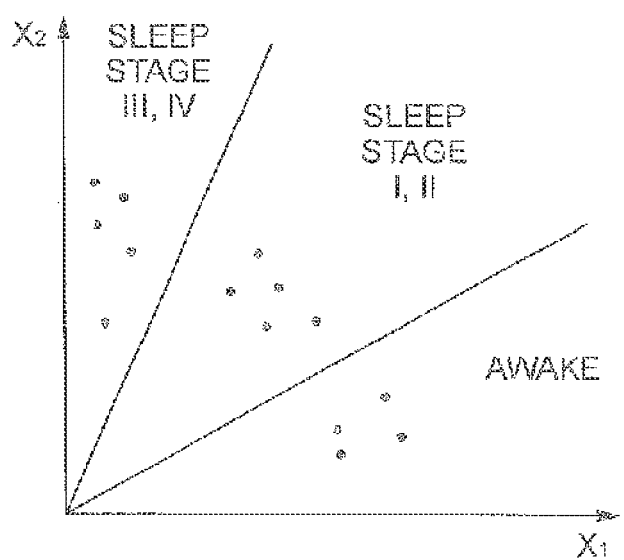
FIG. 6 is a diagram showing a method of estimating a sleep stage based a variable relating to a respiratory waveform using a support vector machine.

In this embodiment, the respiration sensor 12 detects a respiratory waveform B shown in FIG. 4. The wavelength of the respiratory waveform B has variation as shown at t1 to tn of FIGS. 4 and 5. The sleep stage estimation unit 14 plots variables X1 and X2 as a predetermined feature amount for the respiratory waveform B on a vector plane shown in FIG. 6 and estimates the sleep state of the subject by a learning model, such as a support vector machine. The calibration of the learning model may be performed by statistical values obtained by brain wave or the like. The number of variables X1 and X2 may be equal to or greater than three and may be used in a three-dimensional or more vector space.

As the variables X1 and X2 and the like which are the feature amount of the respiratory waveform B, for example, fluctuation in the wavelength t1 to tn for 60 seconds of the respiratory waveform B, the centroid of the wavelength t1 to tn, the mean of the wavelengths t1 to tn, and the standard deviation of the wavelengths t1 to tn, or fluctuation in the amplitude for 60 seconds of the respiratory waveform B, the centroid of the amplitude, the mean of the amplitude, and the standard deviation of the amplitude may be taken.

As the variables X1 and X2 and the like which are the feature amount of the respiratory waveform B, a respiration centroid frequency may be used. This is a value of a frequency component between 0.15 Hz to 0.5 Hz within the respiratory waveform B, and if the respiration centroid frequency becomes a small value from a large value, this represents that the sleep stage becomes a deep stage from a light stage.

The cycle of respiration is 0.15 Hz to 0.5 Hz. That is, single respiration is performed for 6 to 2 seconds. Accordingly, when estimating the feature amount of the respiratory waveform B, such as the respiration centroid frequency, since it is not necessary to perform estimation operation with further resolution, estimation operation of the feature amount of the respiratory waveform B may be performed within this range. In this embodiment, estimation operation for the feature amount of the respiratory waveform B is performed for every 10 seconds, every 20 seconds, every 30 seconds, and every 60 seconds. For example, when an estimated value is output at an interval of 30 seconds, the results estimated for every 10 seconds become an estimation result according to the principle of majority rule, thereby increasing precision. For example, when the estimation results for every 10 seconds are divided into A, A, and B, as an estimated value which is output at an interval of 30 seconds, the estimated value "A" is output according to the principle of majority rule.

As shown in Table 1, for example, the sleep stage estimation unit 14 may set 8 variables which are the mean value of various feature amounts for the respiratory waveform B or 13 variables with the dispersion of various feature amounts of the respiratory waveform B, and may estimate the sleep stage of the subject by a support vector machine in an 8-dimensional vector space or a 13-dimensional vector space of these variables.

TABLE 1

| Mean | Dispersion | Feature Amount | Note | Awake | → Change | Deep Sleep |
|---|---|---|---|---|---|---|
| (1) | (9) | Respiration Centroid Frequency | 0.15 to 0.5 Hz | Large | | Small |

TABLE 1-continued

| Mean | Dispersion | Feature Amount | Note | Awake | → Change | Deep Sleep |
|---|---|---|---|---|---|---|
| (2) | (10) | Inspiratory Volume | Peak Value: R(max) | Large | | Small |
| (3) | | Inspiratory Volume | Fluctuation Coefficient | Large | | Small |
| (4) | | Inspiratory Volume | Change Rate | Large | | Small |
| (5) | (11) | Expiratory Volume/ Inspiratory Volume (I/E) Σv2(t)r2(t)/ Σv1(t)r1(t) | Cell Respiration (Activity) Ventilatory Volume | Large | | Small |
| (6) | (12) | Respiration Rate | | Large | | Small |
| (7) | (13) | Respiration Time | Inter-Peak Time Time for 0.8R(max) | Short | | Long |
| (8) | | Respiration Time | Change Rate | Large | | Small |

Returning to FIG. 2, when the sleep stage of the subject estimated by the sleep stage estimation unit 14 is deeper sleep than the sleep stage II (S104), the sleep quality estimation unit 18 counts AddUpT (S105). Until AddUpT which is the stay time of the deep sleep stage becomes longer than THContinuance which is set to about 90 minutes of the sleep cycle (S106), the sleep quality estimation unit 18 continues to count AddUpT (S104, S105). When AddUpT becomes longer than a value obtained by incrementing THContinuance by 1 (S107), the sleep quality estimation unit 18 increments Status, which is the total number of turns of the cycle of deep sleep, by 1 (S108).

Figure 7:
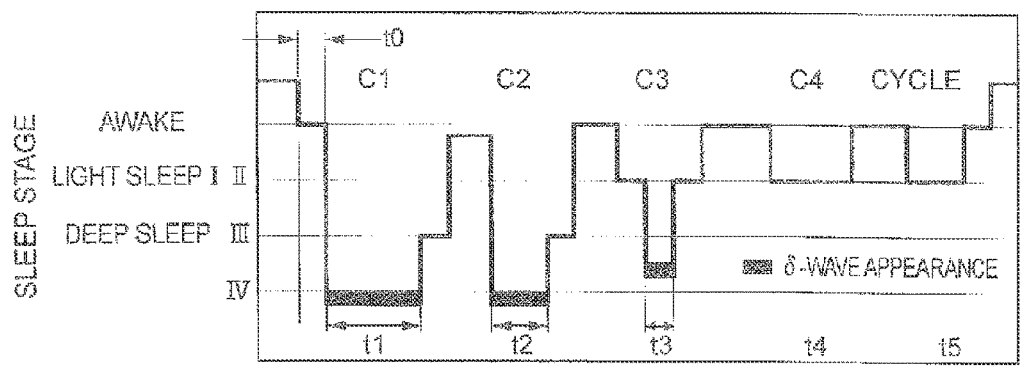
FIG. 7 is a graph showing a sleep stage estimated from a measured value by the respiration sensor.

As shown in FIGS. 3 and 7, in general, when the sleep cycle is too long, the sleep stage becomes light. For this reason, the sleep stage estimation unit 14 determines that the subject is not deep sleeping (S104). The sleep quality estimation unit 18 records AddUpT, which is the stay time in the deep sleep stage, in association with Status, which is the total number of turns of the cycle of deep sleep, and resets AddUpT to 0. In this way, until the wake-up time is reached (S102), the processing of S102 to S109 is executed for each sleep cycle. When the wake-up time is reached (S102), the sleep quality estimation unit 18 estimates the sleep quality of the subject based on the record of AddUpT, which is the stay time in the deep sleep stage, and the models recorded in the sleep rhythm model database 16 (S110).

The sleep quality depends on the accumulated appearance time of δ-wave which appears in the region of deep sleep. In regard to the accumulated appearance time of δ-wave during sleep, in general, the total time every day is substantially a constant value regardless of the number of naps. If a day elapses, the accumulated appearance time of δ-wave for the day returns to the same constant value regardless of the condition of the previous day. It is considered that the sleep quality can be estimated by the accumulated appearance time of δ-wave during sleep. Since an ultradian rhythm which is a human biorhythm has one cycle of about 90 minutes, it may be assumed that the appearance probability of δ-wave fluctuates for the time staying in the deep sleep stage for each sleep cycle.

As shown in FIG. 7, it is assumed that the stay time AddUpT of deep sleep stages (sleep stages deeper than the sleep stage II) of sleep cycles C1 to C4 are t1 to t3. It is known that δ-wave appears for the stay time t1 to t3 of the deep sleep stages. As shown in FIG. 8, in the sleep rhythm model database, the appearance probability of δ-wave of an unspecified number of people for the stay time t1 to t3 correspond to the sleep cycles (cycle) C1 to C4. Accordingly, the sleep quality estimation unit 18 totals the accumulated appearance time of δ-wave for each sleep cycle by Expression (1) to estimate sleep quality Q. However, in Expression (1), p is an arbitrary integer (gain).

[Equation 1]

$$Q = p \times \frac{t_1}{90} \times S_1 + p \times \frac{t_2}{90} \times S_2 + \ldots + p \times \frac{t_n}{90} \times S_n \quad (1)$$

$$Q = \frac{p}{90} \sum_{i=1}^{n} t_i \times S_i,$$

however, $$\sum S_i = 1$$

In the method described in Patent Literature 1, the sleep stage is estimated, the appearance ratio of the sleep stage for an arbitrary unit time is calculated, and the ultradian rhythm of the human is estimated from the appearance ratio. For this reason, since a running mean is calculated by a predetermined threshold value, it is estimated to be excessively "deep sleep", it is often out of the concept that the sleep quality is determined by the appearance time of δ-wave.

According to this embodiment, in the sleep quality estimation device 10, the respiration sensor 12 detects the respiratory waveform of the subject. The sleep stage estimation unit 14 estimates the sleep stage of the subject during sleep based on the respiratory waveform detected by the respiration sensor 12. The sleep rhythm model database 16 records the models associated with the appearance probability of δ-wave for the sleep stage during sleep. The sleep quality estimation unit 18 estimates the appearance time of δ-wave of the subject during sleep based on the sleep stage of the subject during sleep estimated by the sleep stage estimation unit 14 and the models associated with the appearance probability of δ-wave for the sleep stage during sleep recorded in the sleep rhythm model database 16 and estimates the sleep quality of the subject based on the appearance time of δ-wave. For this reason, it is possible to estimate the sleep quality of the subject with higher precision based on the appearance time of δ-wave more closely related to the sleep quality compared to a method which simply accumulates a deep sleep time zone to estimate the sleep quality.

According to this embodiment, the models recorded in the sleep rhythm model database 16 are associated with the appearance probability of δ-wave for the stay time when the sleep stage of each sleep cycle from non-REM sleep to REM sleep stays with a value deeper than the sleep stage II, and the sleep quality estimation unit 18 estimates the stay time of each sleep cycle from the sleep stage of the subject during sleep estimated by the sleep stage estimation unit 14 and estimates the appearance time of δ-wave of the subject during sleep based on the stay time and the models associated with the appearance probability of δ-wave for the stay time of each sleep cycle. There is the stay time when the sleep stage stays with a deep value for each sleep cycle from non-REM sleep to REM sleep, and the appearance probability of δ-wave for the stay time differs for each sleep cycle. For this reason, the appearance time of δ-wave of the subject during sleep is estimated based on the models associated with the appearance probability of δ-wave for the stay time of each sleep cycle, whereby it is possible to estimate the appearance time of δ-wave and to estimate the sleep quality of the subject with higher precision.

According to this embodiment, the respiration sensor 12 detects the respiratory waveform of the subject as the physiological index of the subject. Since the respiratory waveform can be detected in a noncontact state with the skin of the subject, unlike brain wave or heartbeat, it becomes possible to improve the convenience of the subject or to simplify the configuration of the device.

The invention is not limited to the above-described embodiment, and various modifications may be made. For example, in the above-described embodiment, description has been provided focusing on a mode in which the respiration sensor 12, the sleep stage estimation unit 14, the sleep rhythm model database 16, and the sleep quality estimation unit 18 are constituted as the integrated sleep quality estimation device 10. However, the embodiment of the invention also includes a mode in which the physiological index of the subject, such as the respiratory waveform, is measured once and recorded, the sleep stage of the subject is estimated from the respiratory waveform by a separate computer, and the sleep quality of the subject is estimated from the sleep stage and the models in the above-described manner.

Alternatively, the sleep quality estimation device 10 itself may not include the respiration sensor 12, the sleep stage estimation unit 14 may not estimate the sleep stage, and time series information relating to the sleep stage of the subject during sleep shown in FIG. 3 acquired outside the sleep quality estimation device 10 may be merely acquired. In this case, as in the above-described embodiment, the sleep quality estimation unit 18 can estimate the appearance time of δ-wave during sleep of the subject from the time series information of the sleep stage and can estimate the sleep quality of the subject based on the appearance time of δ-wave.

INDUSTRIAL APPLICABILITY

According to the sleep quality estimation device, the sleep quality estimation method, and the program for sleep quality estimation of the embodiment of the invention, it is possible to estimate sleep quality of the subject with higher precision.

REFERENCE SIGNS LIST

10: sleep quality estimation device
12: respiration sensor
14: sleep stage estimation unit
16: sleep rhythm model database
18: sleep quality estimation unit

The invention claimed is:

1. A sleep quality estimation device comprising:
a respiration sensor that detects a respiratory waveform of a subject;
a processor configured to:
estimate a depth of sleep of the subject during sleep based on the detected respiratory waveform of the subject,
estimate an appearance time of δ-wave of the subject during sleep from the estimated depth of sleep of the subject, and
estimate a sleep quality of the subject based on an accumulated appearance time of δ-wave;
a database in which models associated with an appearance probability of δ-wave for the depth of sleep during sleep are recorded, wherein the processor is configured to estimate the appearance time of δ-wave of the subject during sleep based on the depth of sleep of the subject during sleep and the models associated with the appearance probability of δ-wave for the depth of sleep during sleep recorded in the database and to estimate the sleep quality of the subject based on the appearance time of δ-wave, wherein the models recorded in the database are associated with the appearance probability of δ-wave for a stay time when the depth of sleep of each sleep cycle from non-REM sleep to REM sleep stays with a value deeper than a predetermined value, and the processor estimates the stay time of each sleep cycle from the depth of sleep of the subject during sleep and estimates the appearance time of δ-wave of the subject during sleep based on the stay time and the models associated with the appearance probability of δ-wave for the stay time of each sleep cycle, wherein, in the models recorded in the database, the longer the elapsed time from the onset of sleep is, the lower the appearance probability of δ-wave for the sleep depth is set.

2. A sleep quality estimation device comprising:

a respiration sensor that detects a respiratory waveform of a subject;

a processor configured to:
  estimate a depth of sleep of the subject during sleep based on the detected respiratory waveform of the subject,
  acquire a time series information related to the estimated depth of sleep of the subject during sleep,
  estimate an appearance time of δ-wave of the subject during sleep from the depth of sleep of the subject during sleep according to the time series information,
  estimates a sleep quality of the subject based on an accumulated appearance time of δ-wave;

a database in which models associated with an appearance probability of δ-wave for the depth of sleep during sleep are recorded, wherein the processor is configured to estimate the appearance time of δ-wave of the subject during sleep based on the depth of sleep of the subject during sleep and the models associated with the appearance probability of δ-wave for the depth of sleep during sleep recorded in the database and to estimate the sleep quality of the subject based on the appearance time of δ-wave, wherein the models recorded in the database are associated with the appearance probability of δ-wave for a stay time when the depth of sleep of each sleep cycle from non-REM sleep to REM sleep stays with a value deeper than a predetermined value, and the processor estimates the stay time of each sleep cycle from the depth of sleep of the subject during sleep and estimates the appearance time of δ-wave of the subject during sleep based on the stay time and the models associated with the appearance probability of δ-wave for the stay time of each sleep cycle, wherein, in the models recorded in the database, the longer the elapsed time from the onset of sleep is, the lower the appearance probability of δ-wave for the sleep depth is set.

3. A sleep quality estimation method comprising:

detecting, using a respiration sensor, a respiratory waveform of a subject;

estimating, using a processor, a depth of sleep of the subject during sleep based on the detected respiratory waveform;

estimating, using the processor, an appearance time of δ-wave of the subject during sleep from the estimated depth of sleep of the subject;

estimating, using the processor, a sleep quality of the subject based on an accumulated appearance time of δ-wave;

providing a database in which models associated with an appearance probability of δ-wave for the depth of sleep during sleep are recorded;

wherein, in the sleep quality estimating, the appearance time of δ-wave of the subject during sleep is estimated based on the depth of sleep of the subject during sleep and the models associated with the appearance probability of δ-wave for the depth of sleep during sleep recorded in the database;

wherein the models recorded in the database are associated with the appearance probability of δ-wave for a stay time when the depth of sleep of each sleep cycle from non-REM sleep to REM sleep stays with a value deeper than a predetermined value, and in the sleep quality estimating, the stay time of each sleep cycle is estimated from the depth of sleep of the subject during sleep and the appearance time of δ-wave of the subject during sleep is estimated based on the models associated with the appearance probability of δ-wave for the stay time of each sleep cycle, wherein, in the models recorded in the database, the longer the elapsed time from the onset of sleep is, the lower the appearance probability of δ-wave for the sleep depth is set.

4. A sleep quality estimation method comprising:

detecting, using a respiration sensor, a respiratory waveform of a subject;

estimating, by a processor, a depth of sleep of the subject during sleep based on the detected respiratory waveform of the subject;

acquiring, by the processor, a time series information related to the estimated depth of sleep of the subject during sleep;

estimating, by the processor, the appearance time of δ-wave of the subject during sleep from the depth of sleep of the subject during sleep according to the time series information;

estimating, by the processor, a sleep quality of the subject based on an accumulated appearance time of δ-wave;

providing a database in which models associated with an appearance probability of δ-wave for the depth of sleep during sleep are recorded, wherein, in the sleep quality estimating, the appearance time of δ-wave of the subject during sleep is estimated based on the depth of sleep of the subject during sleep and the models associated with the appearance probability of δ-wave for the depth of sleep during sleep recorded in the database and the sleep quality of the subject is estimated based on the accumulated appearance time of δ-wave, wherein the models recorded in the database are associated with the appearance probability of δ-wave for a stay time when the depth of sleep of each sleep cycle from non-REM sleep to REM sleep stays with a value deeper than a predetermined value, and in the sleep quality estimating, the stay time of each sleep cycle is estimated from the depth of sleep of the subject during sleep and the appearance time of δ-wave of the subject during sleep is estimated based on the models associated with the appearance probability of δ-wave for the stay time of each sleep cycle, wherein, in the models recorded in the database, the longer the elapsed time from the onset of sleep is, the lower the appearance probability of δ-wave for the sleep depth is set.

5. A program for sleep quality estimation which causes a computer to execute:

a sleep stage information acquisition step of acquiring time series information relating to a depth of sleep of a subject during sleep; and a sleep quality estimation step of estimating an appearance time of δ-wave of the subject during sleep from the depth of sleep of the subject during sleep according to the time series information acquired in the sleep stage information acquisition step and estimating a sleep quality of the subject based on an accumulated appearance time of δ-wave, wherein the sleep quality estimation step causes the computer to estimate the appearance time of δ-wave of the subject during sleep based on the depth of sleep of the subject during sleep and models associated with an appearance probability of δ-wave for the depth of sleep during sleep recorded in a database and causes the computer to estimate the sleep quality of the subject based on an accumulated appearance time of δ-wave;

wherein the models recorded in the database are associated with the appearance probability of δ-wave for a stay time when the depth of sleep of each sleep cycle from non-REM sleep to REM sleep stays with a value deeper than a predetermined value, and the sleep quality estimation step causes the computer to estimate the stay time of each sleep cycle from the depth of sleep of the subject during sleep and causes the computer to estimate the appearance time of δ-wave of the subject during sleep based on the models associated with the appearance probability of δ-wave for the stay time of each sleep cycle, wherein, in the models recorded in the database, the longer the elapsed time from the onset of sleep is, the lower the appearance probability of δ-wave for the sleep depth is set.

* * * * *